(12) United States Patent
Ichimasa

(10) Patent No.: US 8,919,187 B2
(45) Date of Patent: Dec. 30, 2014

(54) EXHAUST SENSOR ARRANGEMENT STRUCTURE

(75) Inventor: Toshio Ichimasa, Fujisawa (JP)

(73) Assignee: Isuzu Motors Limited, Tokyo (JP)

( * ) Notice: Subject to any disclaimer, the term of this patent is extended or adjusted under 35 U.S.C. 154(b) by 0 days.

(21) Appl. No.: 13/640,808

(22) PCT Filed: Apr. 11, 2011

(86) PCT No.: PCT/JP2011/058992
§ 371 (c)(1),
(2), (4) Date: Oct. 12, 2012

(87) PCT Pub. No.: WO2011/129294
PCT Pub. Date: Oct. 20, 2011

(65) Prior Publication Data
US 2013/0037137 A1   Feb. 14, 2013

(30) Foreign Application Priority Data
Apr. 15, 2010   (JP) .................. 2010-094338

(51) Int. Cl.
*G01M 15/00* (2006.01)
*F01N 13/00* (2010.01)
*G01N 1/22* (2006.01)
*G01N 15/06* (2006.01)

(52) U.S. Cl.
CPC .............. *F01N 13/00* (2013.01); *F01N 13/008* (2013.01); *G01N 1/2252* (2013.01); *G01N 15/0656* (2013.01); *F01N 2560/05* (2013.01)
USPC ....................................................... 73/114.69

(58) Field of Classification Search
CPC ............................ G01M 15/10; G01M 15/102
USPC ........................................................ 73/23.2
See application file for complete search history.

(56) References Cited

U.S. PATENT DOCUMENTS 3,851,632 A * 12/1974 Teshirogi et al. ............. 123/699
3,869,370 A    3/1975 Sayles
(Continued)

FOREIGN PATENT DOCUMENTS

JP    50-28396 A    3/1975
JP    58-172500 A   10/1983
(Continued)

OTHER PUBLICATIONS

PCT Search Report for PCT Serial No. PCT/JP2011/058992 dated May 10, 2011.

(Continued)

*Primary Examiner* — Harshad R Patel
*Assistant Examiner* — Alex Devito
(74) *Attorney, Agent, or Firm* — McCormick, Paulding & Huber LLP

(57) ABSTRACT

Air required for measurement of exhaust gas components is supplied to an exhaust sensor without using a device for generating positive pressure. In a structure for arrangement, in an engine (1), of an exhaust sensor (10) that measures exhaust gas components and requires air for the measurement of the exhaust gas components, an exhaust pipe (5) of the engine (1) communicates with the exhaust sensor (10) through an introduction pipe (15), the exhaust sensor (10) communicates with an intake pipe (2) of the engine (1) through a discharge pipe (16), and an atmosphere pipe (17) open to the atmosphere is connected to the exhaust sensor (10), so that exhaust gas is sucked into the exhaust sensor (10) through the introduction pipe (15) while air is sucked into the exhaust sensor (10) through the atmosphere pipe (17) due to intake negative pressure generated during an intake stroke of the engine (1).

20 Claims, 3 Drawing Sheets

(56) References Cited

U.S. PATENT DOCUMENTS

| | | | |
|---|---|---|---|
| 3,925,989 A * | 12/1975 | Pustelnik | 60/602 |
| 4,441,356 A | 4/1984 | Bohl | |
| 2003/0093994 A1 * | 5/2003 | Bailey | 60/605.2 |
| 2011/0050243 A1 | 3/2011 | Tikkanen | |

FOREIGN PATENT DOCUMENTS

| | | |
|---|---|---|
| JP | 6-43732 Y2 | 11/1994 |
| JP | 2002-340778 A | 11/2002 |
| JP | 2008-111791 A | 5/2008 |
| WO | 2005005964 A1 | 1/2005 |
| WO | 2009/109688 A1 | 9/2009 |

OTHER PUBLICATIONS

European Search Report for European Patent Application No. EP11768815.0 dated Jun. 27, 2014.

* cited by examiner

EXHAUST SENSOR ARRANGEMENT STRUCTURE

CROSS REFERENCE TO RELATED APPLICATIONS

This application is entitled to the benefit of and incorporates by reference essential subject matter disclosed in International Patent Application No. PCT/JP2011/058992 filed on Apr. 11, 2011 and Japanese Patent Application No. 2010-94338 filed Apr. 15, 2010.

TECHNICAL FIELD

This invention relates to a structure for arrangement of an exhaust sensor in an engine, the exhaust sensor being for measuring exhaust gas components and requiring air for the measurement of the exhaust gas components.

BACKGROUND ART

Some exhaust sensors exposed to exhaust gas require air for avoiding contamination with exhaust gas components, or for using the air as a reference in concentration measurement of the exhaust gas components. Such air is supplied in different ways depending on characteristics of the exhaust sensors.

When the exhaust sensor is used as an on-vehicle PM sensor, the PM sensor requires air for measurement of exhaust gas components, and is typically designed on the assumption that the air is supplied to the PM sensor by positive pressure generated by an air compressor or turbo compressor.

One prior art document is WO2009/109688.

DISCLOSURE OF THE INVENTION

However, engines with low engine displacement such as those for passenger cars or small-sized commercial vehicles usually are not provided with an air compressor for generating positive pressure.

Moreover, when using positive pressure generated by a turbo compressor, the exhaust sensor may possibly be contaminated with oil leaked from a sealing portion of the turbo compressor or oil contained in blowby gas.

An object of the invention is therefore to enable an exhaust sensor to be supplied with air required for measurement of exhaust gas components without the need of using a device for generating positive pressure.

In order to achieve the aforementioned object, the invention provides an exhaust sensor arrangement structure which is a structure for arrangement, in an engine, of an exhaust sensor that measures exhaust gas components and requires air for the measurement of the exhaust gas components. In the exhaust sensor arrangement structure, an exhaust pipe of the engine communicates with the exhaust sensor through an introduction pipe, the exhaust sensor communicates with an intake pipe of the engine through a discharge pipe, and an atmosphere pipe open to the atmosphere is connected to the exhaust sensor, so that exhaust gas is sucked into the exhaust sensor through the introduction pipe while the air is sucked into the exhaust sensor through the atmosphere pipe due to intake negative pressure generated during an intake stroke of the engine.

A turbo compressor may be provided in the intake pipe, and the discharge pipe may be connected to the intake pipe on an upstream side of the turbo compressor in terms of flow of intake air.

A turbine for driving the turbo compressor may be provided in the exhaust pipe, and the introduction pipe may be connected to the exhaust pipe on a downstream side of the turbine in terms of flow of the exhaust gas.

An exhaust gas post-treatment apparatus may be provided in the exhaust pipe on the downstream side of the turbine in terms of flow of the exhaust gas, and the introduction pipe may be connected to the exhaust pipe on a downstream side of the exhaust gas post-treatment apparatus in terms of flow of the exhaust gas.

An exhaust gas post-treatment apparatus may be provided in the exhaust pipe on the downstream side of the turbine in terms of flow of the exhaust gas, and the introduction pipe may be connected to the exhaust pipe on an upstream side of the exhaust gas post-treatment apparatus in terms of flow of the exhaust gas.

A metering valve may be provided in the discharge pipe.

A filter may be provided in the atmosphere pipe.

This invention provides an excellent effect that the exhaust sensor can be supplied with air required for measurement of exhaust gas components without using any device for generating positive pressure.

MODE FOR CARRYING OUT THE INVENTION

Preferred embodiments of the invention will be described with reference to the accompanying drawings.

Figure 1:
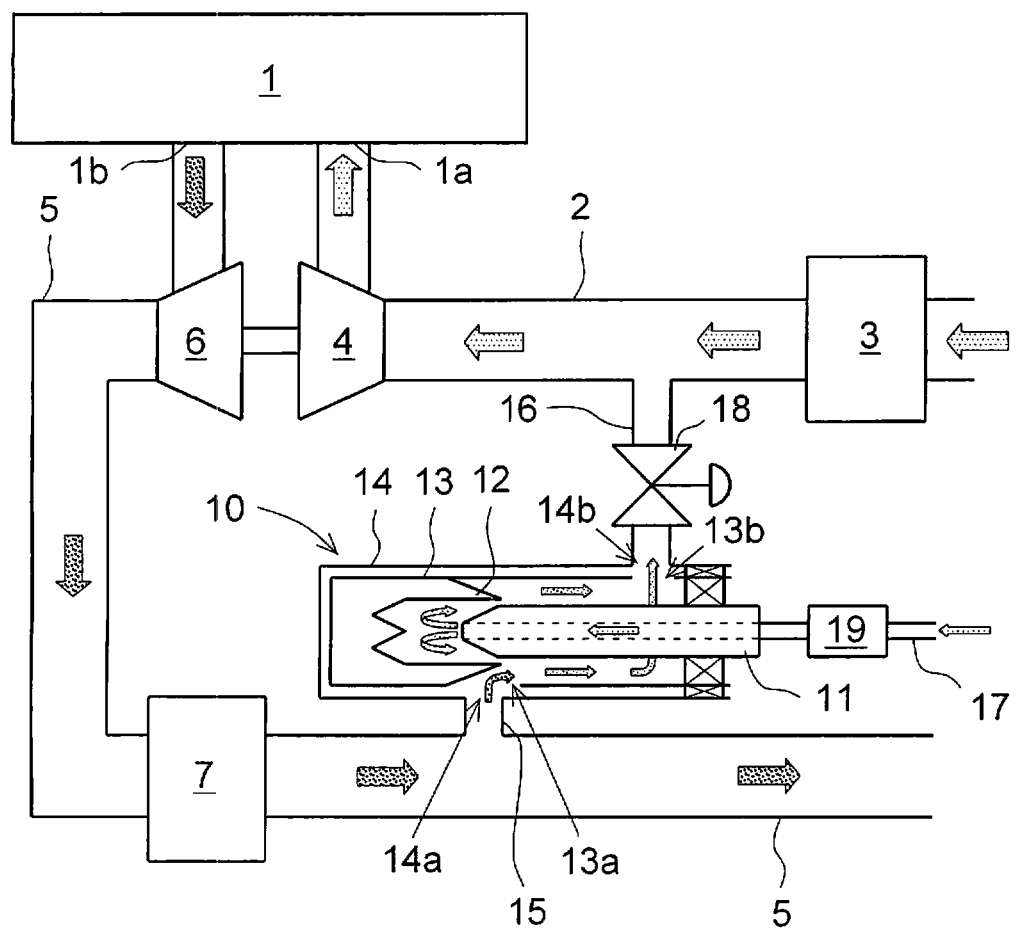
FIG. 1 is a schematic diagram of an engine to which an exhaust sensor arrangement structure according to an embodiment of the invention is applied.

In FIG. 1, the reference numeral 1 denotes an engine (diesel engine in this embodiment), 2 denotes an intake pipe connected to an intake port 1a of the engine 1, 3 denotes an air cleaner provided in the intake pipe 2, 4 denotes turbo compressor (turbo charger compressor) for increasing the pressure of intake air supplied to the engine 1, provided in the intake pipe 2 on the downstream side of the air cleaner 3 in terms of flow of the intake air, 5 denotes an exhaust pipe (tail pipe) connected to an exhaust port 1b of the engine 1, 6 denotes a turbine provided in the exhaust pipe 5 for driving the turbo compressor 4, 7 denotes an exhaust gas post-treatment apparatus provided in the exhaust pipe 5 on the downstream side of the turbine 6 in terms of flow of exhaust gas. The exhaust gas post-treatment apparatus 7 has, for example, a diesel particulate filter (DPF) for collecting particulate matters (PM) contained in the exhaust gas.

The exhaust sensor 10 according to this embodiment is a sensor which can be mounted on a vehicle and is designed on the assumption that the vehicle has an on-board diagnostics (OBD) function. The exhaust sensor 10 is a PM sensor which electrically charges air supplied thereto and detects an emission of particulate matters (PM) based on a variation in electrical charge.

The exhaust sensor 10 according to this embodiment has a nozzle 11 for ejecting air from the front end thereof, a cylindrical or sheath-shaped inner case 13 covering the nozzle 11 and having a throttle portion 12 for throttling the air ejected from the front end of the nozzle 11, a cylindrical or sheath-shaped outer case 14 covering the inner case 13, and an electrode (not shown) for electrically charging the air.

In this embodiment, the nozzle 11, the inner case 13 and the outer case 14 are arranged concentrically with each other. The inner case 13 and the outer case 14 are respectively provided with gas inlets 13a, 14a for introducing the exhaust gas into the inside of the exhaust sensor 10 (into the inside of the inner case 13 according to this embodiment), and gas outlets 13b, 14b for discharging the exhaust gas from the exhaust sensor 10 (from the inner case 13 according to this embodiment). The gas inlets 13a, 14a and the gas outlets 13b, 14b are arranged at intervals in a longitudinal direction of the inner case 13 and the outer case 14.

According to this embodiment, as shown in FIG. 1, the exhaust pipe 5 of the engine 1 communicates with the exhaust sensor 10 through the introduction pipe 15, and the exhaust sensor 10 communicates with the intake pipe 2 of the engine 1 through the discharge pipe 16. An atmosphere pipe 17 open to the atmosphere is connected to the exhaust sensor 10. The discharge pipe 16 is provided with a metering valve 18 for adjusting the flow rate of the exhaust gas and the air supplied to the exhaust sensor 10. The atmosphere pipe 17 is provided with a filter 19 for filtering the air supplied to the exhaust sensor 10. In this embodiment, the atmosphere pipe 17 is connected to the base end of the nozzle 11.

More specifically, according to the embodiment, one end of the introduction pipe 15 is connected to the exhaust pipe 5 on the downstream side of the exhaust gas post-treatment apparatus 7 in terms of flow of the exhaust gas, while the other end of the introduction pipe 15 is connected to the inner case 13 and outer case 14 (the gas inlets 13a, 14a) of the exhaust sensor 10. One end of the discharge pipe 16 is connected to the inner case 13 and outer case 14 (the gas outlets 13b, 14b) of the exhaust sensor 10, and the other end of the discharge pipe 16 is connected to the intake pipe 2 on the upstream side of the turbo compressor 4 in terms of flow of the exhaust gas (in the example shown in FIG. 1, connected to the intake pipe 2 between the turbo compressor 4 and the air cleaner 3).

Operation of the embodiment will be described below.

According to this embodiment, the exhaust sensor 10 is arranged between an engine air-intake system and an engine exhaust system. Specifically, the exhaust sensor 10 communicates with the intake pipe 2 of the engine 1 through the discharge pipe 16, and communicates with the exhaust pipe 5 of the engine 1 through the introduction pipe 15. Accordingly, the air (atmosphere) is sucked toward the intake port 1a of the engine 1 from the air cleaner 3 and the filter 19 due to negative pressure generated within the intake pipe 2 during an intake stroke of the engine 1. The air sucked in from the filter 19 is supplied to the inside of the exhaust sensor 10 through the atmosphere pipe 17.

The engine exhaust system (the exhaust pipe 5 of the engine 1) communicates with the exhaust sensor 10 through the introduction pipe 15. Therefore, the exhaust gas within the exhaust pipe 5 of the engine 1 is also sucked toward the intake port 1a of the engine 1 due to negative pressure generated in the inside of the intake pipe 2 during an intake stroke of the engine 1. The sucked-in exhaust gas is supplied to the inside of the exhaust sensor 10 through the introduction pipe 15.

According to the embodiment, in other words, the exhaust pipe 5 of the engine 1 communicates with the exhaust sensor 10 through the introduction pipe 15, the exhaust sensor 10 communicates with the intake pipe 2 of the engine 1 through the discharge pipe 16, and the atmosphere pipe 17 open to the atmosphere is connected to the exhaust sensor 10, so that the exhaust gas is sucked into the exhaust sensor 10 through the introduction pipe 15 and the air is sucked into the exhaust sensor 10 through the atmosphere pipe 17 due to intake negative pressure generated during an intake stroke of the engine 1. This makes it possible to supply the exhaust sensor 10 with air required for measurement of exhaust gas components without the need of using any device for generating positive pressure.

According to the embodiment, further, the turbo compressor 4 is provided in the intake pipe 2 and the discharge pipe 16 is connected to the intake pipe 2 on the upstream side of the turbo compressor 4 in terms of flow of the intake air, which makes it easy to generate a pressure difference between the introduction pipe 15 and the discharge pipe 16. As a result, the exhaust gas and the air can be efficiently supplied to the inside of the exhaust sensor 10.

Further, according to the embodiment, the metering valve 18 is provided in the discharge pipe 16, so that the pressure difference between the introduction pipe 15 and the discharge pipe 16 can be varied by this metering valve 18. This makes it possible to appropriately adjust the flow rate of the exhaust gas and the air supplied into the exhaust sensor 10.

Although the invention has been described in its preferred form, it should be understood that the invention is not limited to the embodiment described above, and various modifications and variations are possible.

Figure 2:
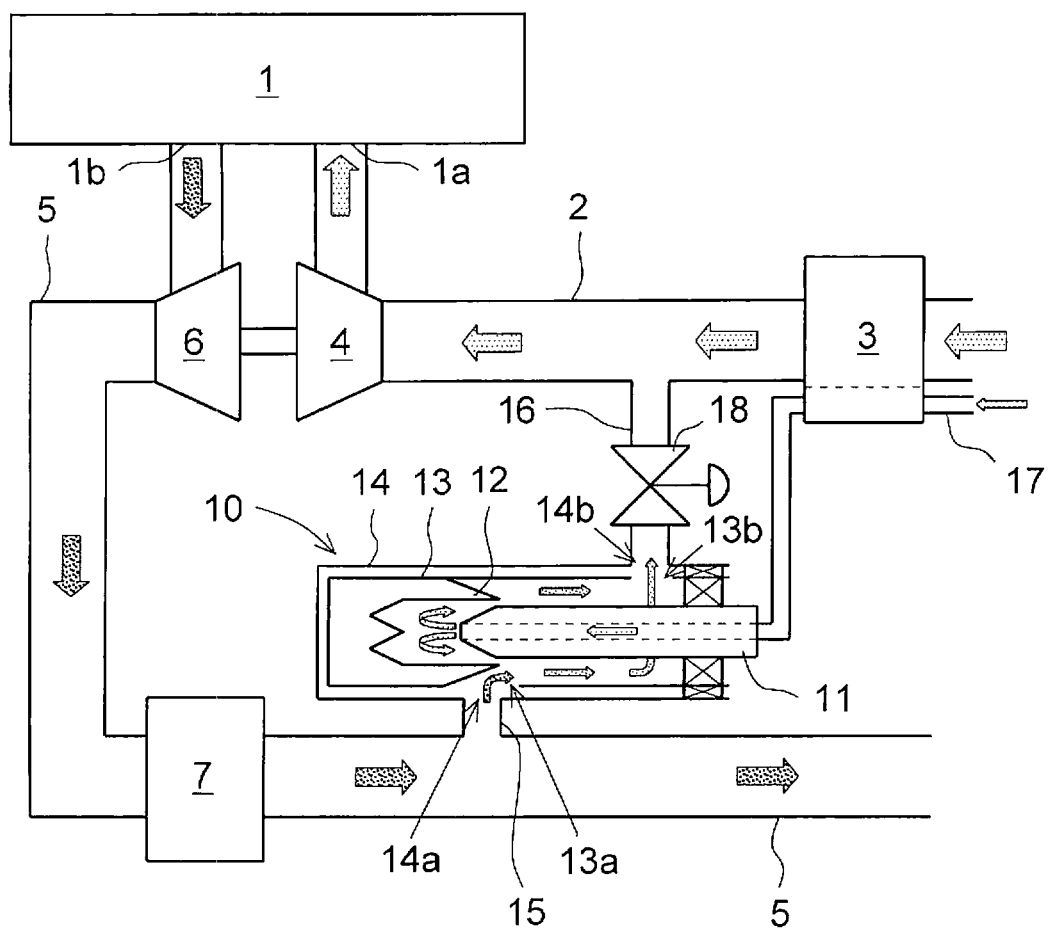
FIG. 2 is a schematic diagram of an engine to which an exhaust sensor arrangement structure according to another embodiment of the invention is applied.

For example, although in the embodiment described above, the filter 19 for filtering the air supplied to the exhaust sensor 10 is provided independently from the air cleaner 3, the air cleaner 3 can be shared by the intake pipe 2 and the atmosphere pipe 17, as shown in FIG. 2, when an adequate negative pressure is generated by air intake resistance or the like.

Figure 3:
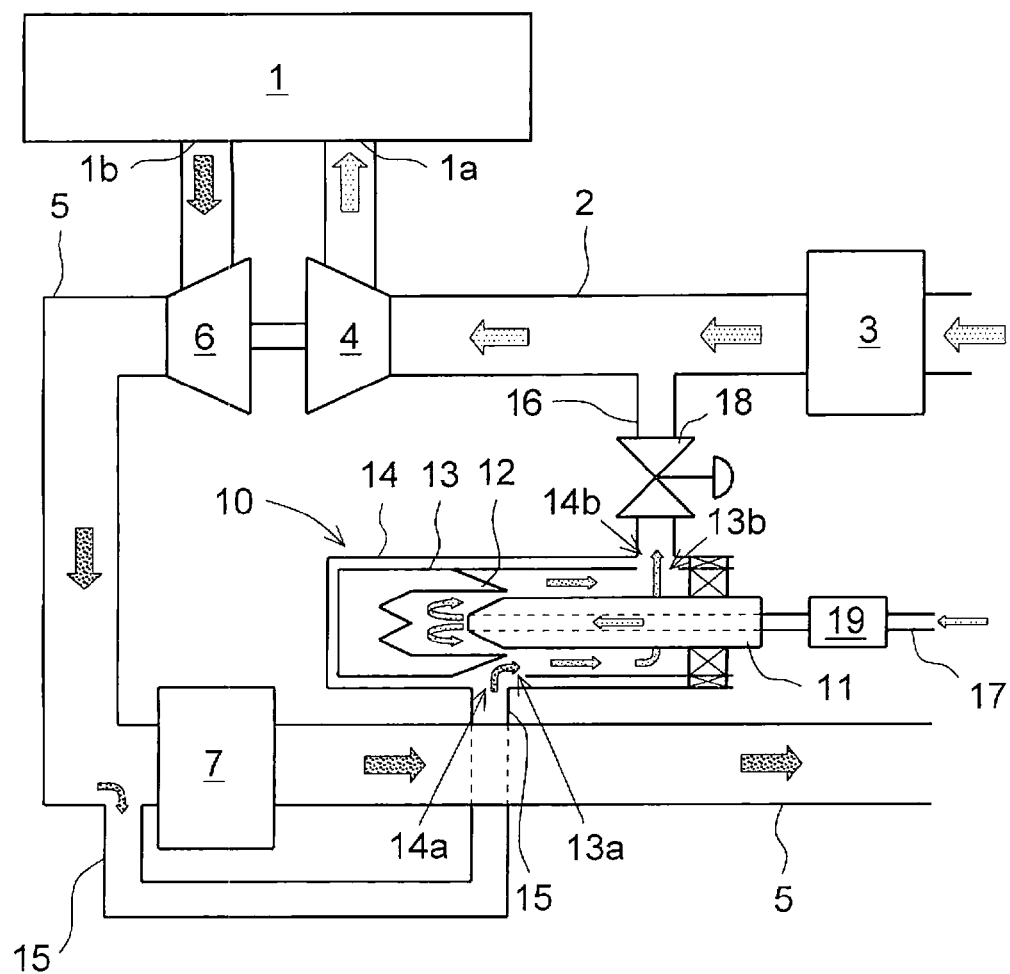
FIG. 3 is a schematic diagram of an engine to which an exhaust sensor arrangement structure according to still another embodiment of the invention is applied.

Further, depending on characteristics of the exhaust sensor 10, as shown in FIG. 3, the point where the introduction pipe 15 communicates can be shifted to a point of the exhaust pipe 5 on the upstream side of the exhaust gas post-treatment apparatus 7 in terms of flow of the exhaust gas. This means that one end of the introduction pipe 15 can be connected to the exhaust pipe 5 on the upstream side of the exhaust gas post-treatment apparatus 7 in terms of flow of the exhaust gas.

Furthermore, the exhaust sensor 10 is not limited to a PM sensor, but may be any other sensor for measuring exhaust gas components other than PM as long as it requires air.

Although the invention above has been described in connection with preferred embodiments of the invention, it will be evident for a person skilled in the art that several modifications are conceivable without departing from the invention as defined by the following claims.

What is claimed is:

1. An exhaust sensor arrangement structure comprising:
   an air-intake pipe of an engine;
   an exhaust pipe of the engine;
   an exhaust sensor arranged between the air-intake pipe and the engine exhaust pipe;
   an atmosphere pipe having one end thereof connected to the exhaust sensor and another end thereof open to the atmosphere;
   an introduction pipe having one end thereof connected to the exhaust pipe and another end thereof connected to the exhaust sensor; and
   a discharge pipe having one end thereof connected to the exhaust sensor and another end thereof connected to the intake pipe;
   wherein the exhaust gas is sucked into the exhaust sensor through the introduction pipe and the air that is required for measurement of exhaust gas components is sucked directly into the exhaust sensor from the atmosphere through the atmosphere pipe due to intake negative pressure generated during an intake stroke of the engine.

2. The exhaust sensor arrangement structure according to claim 1, wherein a turbo compressor is provided in the intake pipe, and the discharge pipe is connected to the intake pipe on an upstream side of the turbo compressor in terms of flow of intake air.

3. The exhaust sensor arrangement structure according to claim 2, wherein a turbine for driving the turbo compressor is provided in the exhaust pipe, and the introduction pipe is connected to the exhaust pipe on a downstream side of the turbine in terms of flow of the exhaust gas.

4. The exhaust sensor arrangement structure according to claim 3, wherein an exhaust gas post-treatment apparatus is provided in the exhaust pipe on the downstream side of the turbine in terms of flow of the exhaust gas, and the introduction pipe is connected to the exhaust pipe on a downstream side of the exhaust gas post-treatment apparatus in terms of flow of the exhaust gas.

5. The exhaust sensor arrangement structure according to claim 4, wherein a metering valve is provided in the discharge pipe.

6. The exhaust sensor arrangement structure according to claim 5, wherein a filter is provided in the atmosphere pipe.

7. The exhaust sensor arrangement structure according to claim 4, wherein a filter is provided in the atmosphere pipe.

8. The exhaust sensor arrangement structure according to claim 3, wherein an exhaust gas post-treatment apparatus is provided in the exhaust pipe on the downstream side of the turbine in terms of flow of the exhaust gas, and the introduction pipe is connected to the exhaust pipe on an upstream side of the exhaust gas post-treatment apparatus in terms of flow of the exhaust gas.

9. The exhaust sensor arrangement structure according to claim 8, wherein a metering valve is provided in the discharge pipe.

10. The exhaust sensor arrangement structure according to claim 9, wherein a filter is provided in the atmosphere pipe.

11. The exhaust sensor arrangement structure according to claim 8, wherein a filter is provided in the atmosphere pipe.

12. The exhaust sensor arrangement structure according to claim 3, wherein a metering valve is provided in the discharge pipe.

13. The exhaust sensor arrangement structure according to claim 12, wherein a filter is provided in the atmosphere pipe.

14. The exhaust sensor arrangement structure according to claim 3, wherein a filter is provided in the atmosphere pipe.

15. The exhaust sensor arrangement structure according to claim 2, wherein a metering valve is provided in the discharge pipe.

16. The exhaust sensor arrangement structure according to claim 15, wherein a filter is provided in the atmosphere pipe.

17. The exhaust sensor arrangement structure according to claim 2, wherein a filter is provided in the atmosphere pipe.

18. The exhaust sensor arrangement structure according to claim 1, wherein a metering valve is provided in the discharge pipe.

19. The exhaust sensor arrangement structure according to claim 18, wherein a filter is provided in the atmosphere pipe.

20. The exhaust sensor arrangement structure according to claim 1, wherein a filter is provided in the atmosphere pipe.

* * * * *